US00PP09925P

United States Patent [19]

Jones

[11] Patent Number: Plant 9,925

[45] Date of Patent: Jun. 17, 1997

[54] BLACK WALNUT TREE NAMED HPC-120

[75] Inventor: James E. Jones, Stockton, Mo.

[73] Assignee: Hammons Products, Stockton, Mo.

[21] Appl. No.: 618,280

[22] Filed: Mar. 18, 1996

[51] Int. Cl.[6] ..... A01H 5/00

[52] U.S. Cl. ..... Plt./32

[58] Field of Search ..... Plt./32

*Primary Examiner*—James R. Feyrer

*Attorney, Agent, or Firm*—Dressler, Rockey, Milnamow & Katz

[57] ABSTRACT

A new and distinct cultivar of American black walnut (*Juglans nigra L.*) that is large compared to other black walnut trees, is a vigorous grower and appears resistant to many foliar diseases. The tree is also an excellent nut producer.

6 Drawing Sheets

BACKGROUND OF THE INVENTION

This invention relates to a new and distinct variety of American black walnut tree (*Juglans nigra L.*).

In 1976, I planted a variety of seedlings that I obtained from the Missouri State Nursery in Licking along with some additional seedlings I had in a plantation in Cedar County, Miss. The seedlings I obtained from the Missouri State Nursery were approximately one year old and were labeled as "super seedlings" or "nursery run" . As the trees developed and began to bear fruit, I recognized that the parent tree of this invention had improved characteristics. My interest and experience with American black walnut trees led me to realize that this tree was a unique and distinct development.

REPRODUCTION

Subsequently in 1990, I asexually reproduced the tree of the present invention taking scions from the parent tree and grafting these on to an unpatented American black walnut tree stock in Cedar County, Miss. The asexual reproductions ran true to the parent tree and to each other in all respects.

The botanical details of this new and distinct variety of American black walnut tree will now be described using data collected from the parent tree for over a significant period of time.

DETAILED DESCRIPTION OF THE INVENTION

Figure 1:
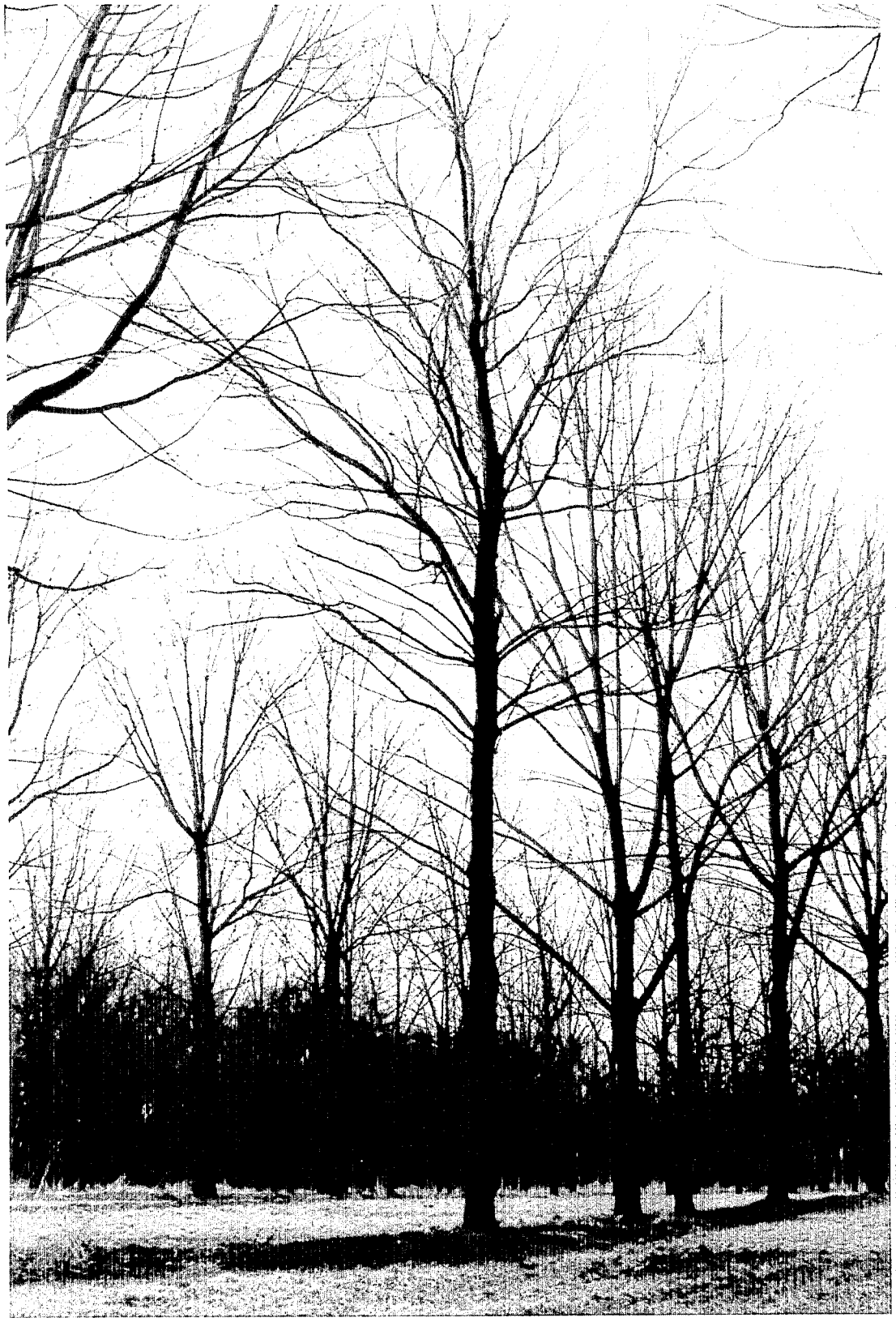
FIG. 1 is a photograph showing the timber form of parent tree of this invention at age 20.
Figure 2:
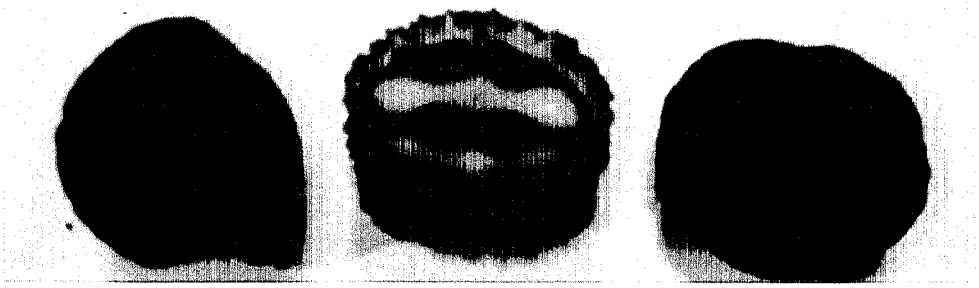
FIG. 2 is a photograph showing the nuts from the parent tree of this invention.

Tree: The tree is large when compared to other black walnut trees of this species. The tree is a vigorous grower, and is a very heavy producer. Additionally, the tree produces a long bole. The tree is approximately 62 feet high, has a diameter of 13.8 inches at breast height (dbh), and a spread of approximately 38 feet. The tree is an early bearer but not annually. However, the annual bearing characteristic may be masked by site and environmental conditions during flowering.

Trunk: The trunk of the tree is like that of other black walnut trees for this species. However, the bark tends to be less deeply grooved, not as thick and has thinner ridges. The old bark is gray to light brown in color and has a rough texture that tends to be less thick than average. In contrast, the new bark is light brown in color, has a smooth texture and has a moderate to thin thickness.

Branches: The form of the branches is the same as other black walnut trees of this species. The lateral branches tend to be smaller in diameter and at more of a right angle to the trunk than lateral branches on other black walnut trees of this species. Additionally, the branches have a relatively smooth texture.

Stems: The stems are like the stems of other black walnut trees of this species. The stems have hair and are light brown in color.

Leaves: The tree has an abundant quantity of leaves which are arranged in a pinnately compound fashion. The leaves are approximately 35 to 40 cm in length and approximately 13 to 16 cm in width. There are approximately 14–16 dark green leaflets per leaf which are approximately 6 to 10 cm in length and 2.0 to 3.0 cm in width. Furthermore, the leaflets are relatively smooth on top with a light pubescence on the bottom. While the leaflets are narrow lanceolate in shape, they are pointed at the apices. The base of the leaflet varies from rounded to heart shaped to pointed in shape. The leaflets have a smooth texture with a serrated margin and venation typical of that found in black walnut trees of this species. The leaflets change colors from green to yellow in the fall.

Leafing date: The bud breaks from April 20–April 28.

Inflorescence: The tree is precocious. Pistillate and staminate flowers are usually produced early, within 8 to 10 years. One to three pistillate flowers are present per bearing site on the flowering tip. The female flower is not inconspicuous and has basically the same appearance as other individuals of the species, as receptivity advances, the flower color changes from light green to rose. The first female bloom is between May 1–May 7. The peak female bloom is near May 10. The last female bloom is by May 16. The first male bloom is between April 24–April 30. The peak male bloom is between May 6 to May 11. The last male bloom is May 14–May 20. The first pollen is shed between May 1–May 3. Generally, the pollen is shed for approximately 12 days. The last pollen shed is May 14–May 20. The length of the female flower is ⅜–⅝inch and the length of the male flower 3–4 inches. The male and female flowers are not unlike the typical black walnut flower for this species. The female flower turns from light green to rose as receptivity advances.

Husk: The husk is somewhat pear shaped and pendulous, has no sutures and is thick. The outer surface of the nut is somewhat rough. Prior to harvest, the husk is light green to dark green in color. At harvest, the husk may be dark green. Additonally, the husk does not open freely and does not have a splitting tendency.

Nut: The nut is large in size and has an average length of 1 7/16 inches and an average width of approximately 1 9/16 inches from cheek to cheek and 1 5/16 inches from suture to suture. The average weight of the nut is 21.4 grams and the number of nuts per ounce is 0.75. In addition to being somewhat rectangular to pear shaped, the nut is light brown in color and has an inner shell and outer shell. The outer shell is relatively thick and has a corrugated texture. The percentage of kernal to nut is 19.6%.

Figure 3:
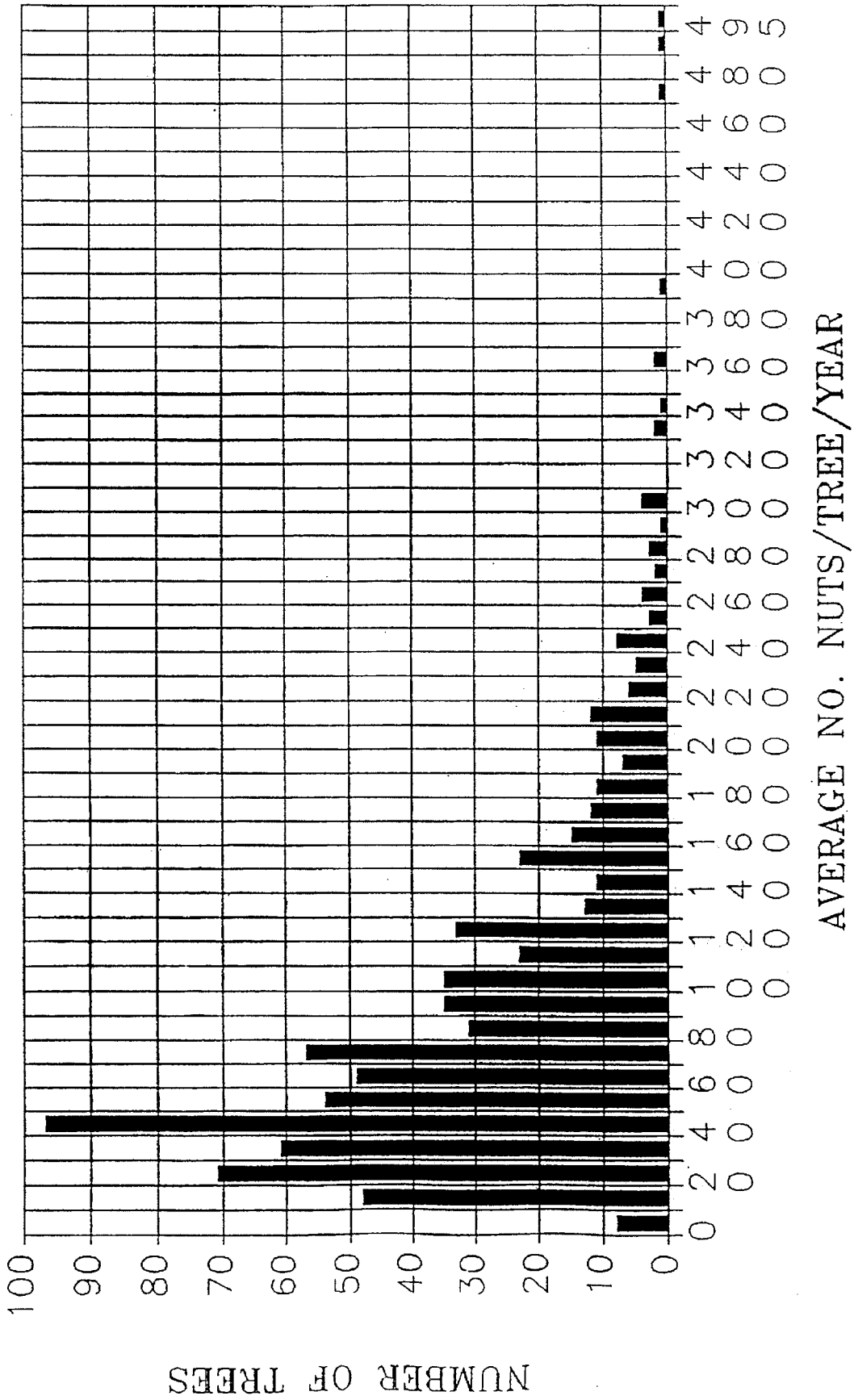
FIG. 3 is a bar graph of the walnut bearing characteristics of the parent tree of this invention with 762 other black walnut trees grown in the same block/area.

FIG. 3 depicts all of the trees growing in the block/area where the parent tree is growing. The 763 black walnut trees were originally planted in 1976 at Hammons Sho-Neff Plantation in Stockton, Miss. in well-drained, fertile river-bottom soil and spaced 10'×40' apart from one another. The FIG. 3 illustrates the huge variation in nut bearing capabilities of the species. The parent tree of this invention is represented by the short vertical bar on the far right side of the graph and produces an average of 495 nuts per year (the nuts were harvested from 1986–1990).

Kernel: The kernel is larger than average. The lobe has an average length between ¾–⅞ inches, an average width between ½–⅝ inches and an average thickness of 3/16–¼ inches. The kernel is brown in color and has a smooth to somewhat corrugated texture. Additionally, the shape of the kernal is typical of that for black walnut trees of these species. The average weight of a kernel in a nut is 4.2 grams.

Harvest: The nuts are generally ready for harvest between October 5 to October 20. No special conditions are needed for harvesting. The nuts are simply picked up by hand as they mature and fall to the ground naturally. Once harvested, the nuts are counted and the husk removed. The nuts are then weighed and then air dried.

Disease resistance: Appears to be resistant to most foliar diseases.

Growing conditions: Excellent, well-drained, fertile, river bottom soil. Huntington soil series.

Isoelectric focusing: Isoelectric focusing was conducted on the parent tree of this invention as well as the parent tree of HPC-148 (U.S. Ser. No. 08/617,047) and STW-13 (U.S. Ser. No. 08/617,625) by Isolab, Inc., Akron, Ohio, to develop an enzyme profile for these trees. The procedure used is described below.

*Sample preparation.*—Ten individual leaves from the parent tree was homogenized with an enzyme extraction solution. The samples were allowed to incubate at 4°–8° C. overnight. The samples were then centrifuged and the resulting supernant was ready for electrophoresis in a pH gradient.

*Isoelectric focusing.*—The supernant was run through a broad-ranged (pH 3–10) HyPure Gel (Isolab, Inc., Akron, Ohio). After protein separation, isozyme staining was performed for selected proteins. The stains used were selective for the following 8 enzymes: acid phosphatase, malic enzyme, diaphorase, esterase, alcohol dehydrogenase, isocitric dehydrogenase, malate dehydrogenase and peroxidase. These enzymes were selected because they are useful for showing the differences between varieties. Acid phosphatase, malic enzyme and diaphorase were chosen for further examination because these three enzymes gave the most intensity.

Figure 4:
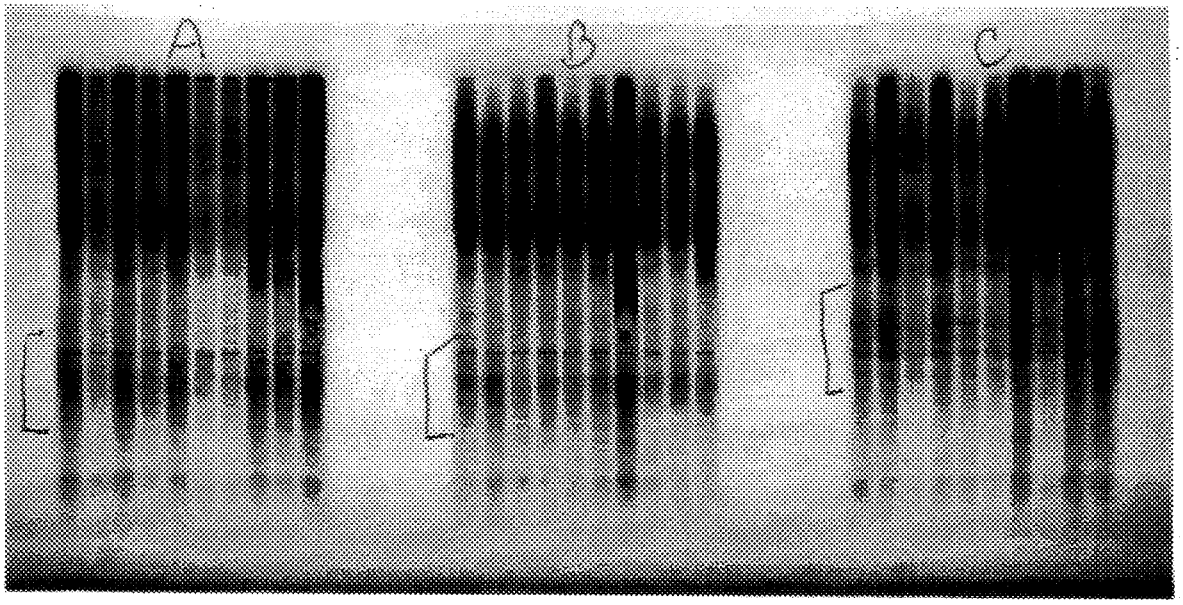
FIG. 4 contains three electrophoresis gels resulting from isoelectric focusing. The enzyme acid phosphatase was used to establish in enzyme pattern for the parent tree of this invention and other trees.

*Results.*—As shown in FIG. 4, the parent tree of this invention and the parent tree of HPC-148 gave the same pattern for the acid phosphatase. The parent tree of STW-13 gave a different pattern. The parent tree of this invention is shown in B, HPC-148 is shown in A, STW-13 is shown in C. Each lane represents an individual leaf sample.

Figure 5:
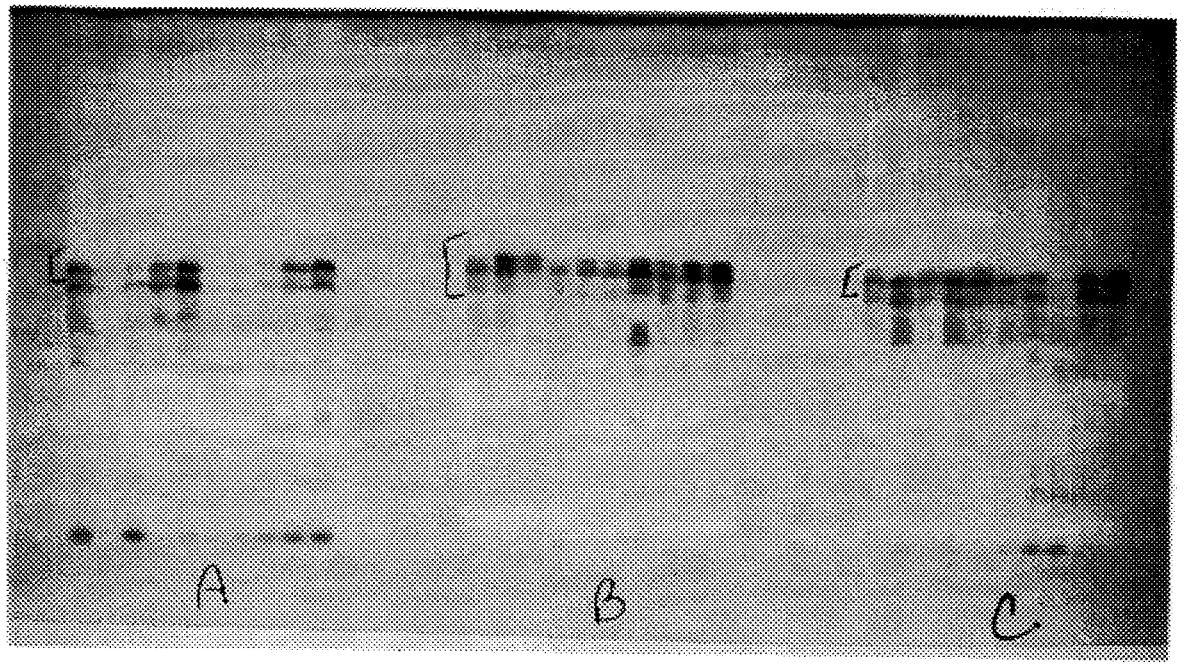
FIG. 5 contains three electrophoresis gels resulting from isoelectric focusing. The enzyme used was the malic enzyme.

As shown in FIG. 5, the parent tree of HPC-148 and the parent tree of STW-13 gave single pattern when tested with the malic enzyme. The parent tree of this invention gave a double pattern. The parent tree of this invention is shown in B, HPC-148 is shown in A and STW-13 is shown in C.

Figure 6:
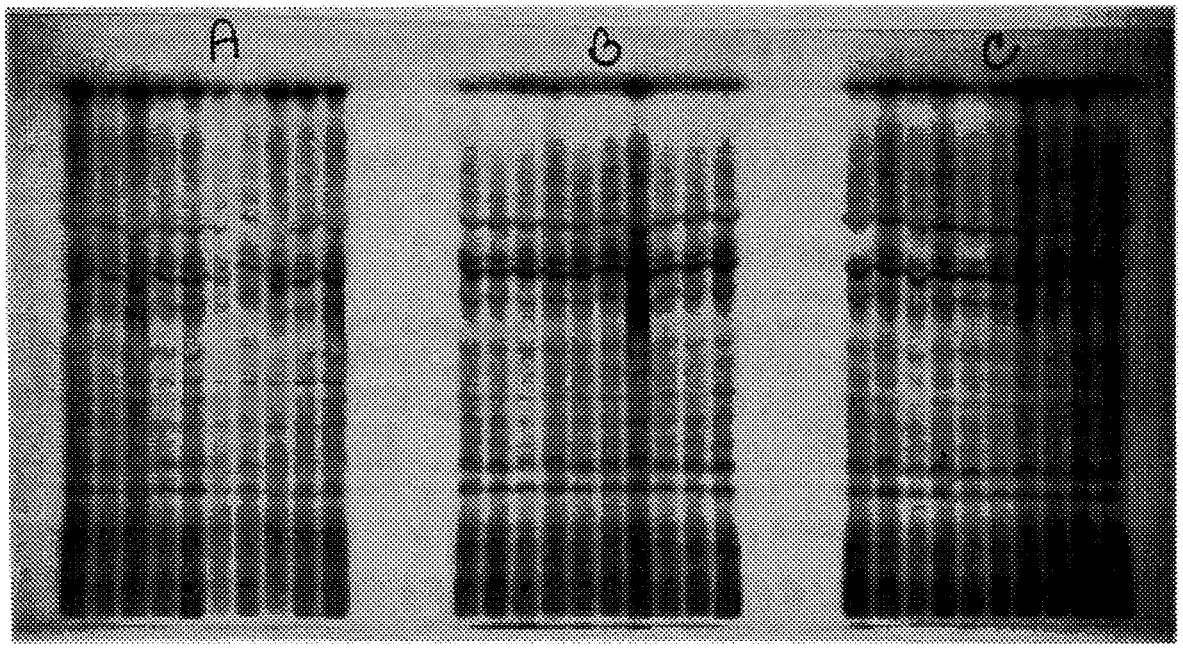
FIG. 6 contains three electrophoresis gels resulting from isoelectric focusing. The enzyme used was diaphorase.

As shown in FIG. 6, all of the trees gave the same exact enzyme pattern with for the diaphorase. The parent tree of this invention is shown in B, HPC-148 is shown in A and STW-13 is shown in C.

Therefore, these three trees can be differentiated using the acid phosphatase and the malic enzyme patterns.

I claim:

1. The new and distinct variety of black walnut tree herein described and illustrated and identified by the characteristics enumerated above.

* * * * *

UNITED STATES PATENT AND TRADEMARK OFFICE

CERTIFICATE OF CORRECTION

PATENT NO. : Plant 9,925

DATED : June 17, 1997

INVENTOR(S) : James E. Jones

It is certified that error appears in the above-indentified patent and that said Letters Patent is hereby corrected as shown below:

In column 1, line 38, please replace "in" with --an--.

In column 3, line 4, after "flower" please insert --is--.

Signed and Sealed this

Ninth Day of December, 1997

*Attest:*

Bruce Lehman

BRUCE LEHMAN

*Attesting Officer*

*Commissioner of Patents and Trademarks*